United States Patent [19]

Turnbull et al.

[11] Patent Number: 5,218,970
[45] Date of Patent: Jun. 15, 1993

[54] TRACHEAL TUBE CUFF PRESSURE MONITOR

[75] Inventors: Christopher S. Turnbull, Hythe; Brian Crawley, Canterbury, both of England

[73] Assignee: Smiths Industries Public Limited Company, London, England

[21] Appl. No.: 799,840

[22] Filed: Dec. 2, 1991

[30] Foreign Application Priority Data

Dec. 5, 1990 [GB] United Kingdom ............... 9026403

[51] Int. Cl.$^5$ ............................................... A61B 5/00
[52] U.S. Cl. ............................... 128/748; 128/207.15; 128/630; 128/774; 128/782; 137/557; 604/100
[58] Field of Search ................. 128/207.15, 748, 630, 128/675, 774, 780, 782; 137/557; 604/100

[56] References Cited

U.S. PATENT DOCUMENTS

| | | | |
|---|---|---|---|
| 3,989,571 | 11/1976 | Harautuneian | 128/207.15 |
| 4,134,407 | 1/1979 | Elam | |
| 4,160,448 | 7/1979 | Jackson | 128/673 |
| 4,174,637 | 11/1979 | Mulzet et al. | 73/730 |
| 4,185,638 | 1/1980 | Bruner | 128/207.15 |
| 4,285,340 | 8/1981 | Gezari et al. | 128/207.15 |
| 4,719,796 | 1/1988 | Zenker | |
| 4,872,483 | 10/1989 | Shah | |
| 5,016,466 | 5/1991 | Ness et al. | 73/4 R |

FOREIGN PATENT DOCUMENTS

| | | |
|---|---|---|
| 0355373 | 2/1990 | European Pat. Off. |
| 0396353 | 11/1990 | European Pat. Off. |
| 8804042 | 6/1988 | PCT Int'l Appl. |
| 1436313 | 5/1976 | United Kingdom |
| 2174303 | 11/1986 | United Kingdom |

Primary Examiner—Randall L. Green
Assistant Examiner—Paul Prebilic
Attorney, Agent, or Firm—Pollock, Vande Sande & Priddy

[57] ABSTRACT

A monitor for measuring the pressure in the cuff on a tracheal tube is clipped onto a coupling at the end of an inflation indicator balloon that communicates with the cuff. The monitor has a silicon strain gauge pressure sensor and a spring that urges the sensor resiliently against one side of the balloon, the other side of the balloon resting on a base plate. The monitor has a numeric display connected to the sensor on which a representation of pressure in the indicator balloon and hence in the cuff is displayed.

8 Claims, 1 Drawing Sheet

TRACHEAL TUBE CUFF PRESSURE MONITOR

BACKGROUND OF THE INVENTION

This invention relates to cuff pressure monitors and tube assemblies.

The invention is more particularly concerned with pressure monitors for measuring the pressure in cuffed medico-surgical tubes, such as endotracheal tubes or tracheostomy tubes.

Tracheal tubes are used to transmit anaesthetic or ventilation gases to a patient, such as during surgery, or to provide an airway to the trachea when the patient is breathing spontaneously. These tubes often have a cuff around the tube close to the patient end which is inflated to seal with the trachea so that gas flow is confined within the tube. The cuff is inflated and deflated via a small-bore lumen extending along the tube within its wall which opens into the cuff close to the distal or patient end, and is connected to one end of an inflation line close to the proximal or machine end of the tube. The other end of the inflation line extends outside the patient and has a connector and an inflation indicator in the form of an inflatable balloon the interior of which communicates with the interior of the inflation line. The cuff is initially deflated and, after insertion of the tube into the trachea, is inflated by means of a syringe or similar device coupled to the connector, which administers a measured volume of air. This causes inflation of the cuff and the indicator. The indicator provides visual evidence to the clinician of the state of inflation of the cuff.

These tubes may remain in place for some time and the pressure within the cuff can change during this time. The pressure may increase because of diffusion of anaesthetic gases through the wall of the cuff. Alternatively, the pressure may decrease because of leakage. Although the inflation balloon indicates large changes in pressure of the cuff, it is not very sensitive to small changes in pressure. It is desirable to be able to maintain the cuff at the correct pressure because too high a pressure can lead to damage to the tracheal lining, whereas too low a pressure can allow leakage of gas between the tube and the trachea. Pressure gauges are available which can be coupled to the connector at the machine end of the inflation line but these are generally bulky and expensive. Their size and weight make them unsuitable for attachment to a tube long term.

SUMMARY OF THE INVENTION

It is an object of the present invention to provide an alternative pressure monitor which can be used to monitor cuff pressure.

According to one aspect of the present invention there is provided a cuff pressure monitor for use on a cuffed medico-surgical tube of the kind for insertion into a body cavity and having a flexible inflation indicator located externally of the body which communicates with the cuff and is inflated on inflation of the cuff, the monitor being adapted to be attached with the inflation indicator and having pressure sensor means that contacts the exterior of the inflation indicator such that change in inflation of the indicator causes a change in the output of the pressure sensor means, and the monitor includes display means arranged to receive the output of the pressure sensor means and to provide a display representation indicative of pressure in the cuff.

The inflation indicator is preferably a flexible balloon. The monitor may be removable from the inflation indicator and may be adapted for use with a cuffed medico-surgical tube of the kind in which the inflation indicator is provided at one end of a coupling by which fluid can be supplied to the cuff, the pressure monitor being adapted to clip onto the coupling. The monitor may include a plate extending on one side of the inflation indicator and a means resiliently urging the pressure sensor means in contact with the opposite side of the inflation indicator. The pressure sensor means is preferably an electrical pressure sensor such as one including a silicon strain gauge. The display is preferably a numeric display and may be a liquid crystal display.

According to another aspect of the present invention there is provided a medico-surgical tube having an inflatable cuff close to one end which is in use adapted to seal the tube with a body cavity within which the one end of the tube is inserted, and a flexible inflation indicator which communicates with the cuff and is inflated on inflation of the cuff, the inflation indicator in use being located externally of the body cavity; and a cuff pressure monitor according to the above one aspect of the invention attached with the inflation indicator.

According to a further aspect of the present invention there is provided a tracheal tube assembly comprising: a tracheal tube having an inflatable cuff close to one end which is adapted in use to seal the tube with the trachea, and a flexible inflation indicator which communicates with the cuff and is inflated on inflation of the cuff, the inflation indicator in use being located externally of the patient; and a cuff pressure monitor according to the above one aspect of the invention attached with the inflation indicator.

A cuff pressure monitor and a tube assembly including the monitor in accordance with the present invention, will now be described, by way of example, with reference to the accompanying drawings.

DESCRIPTION OF THE PREFERRED EMBODIMENTS

Figure 1:
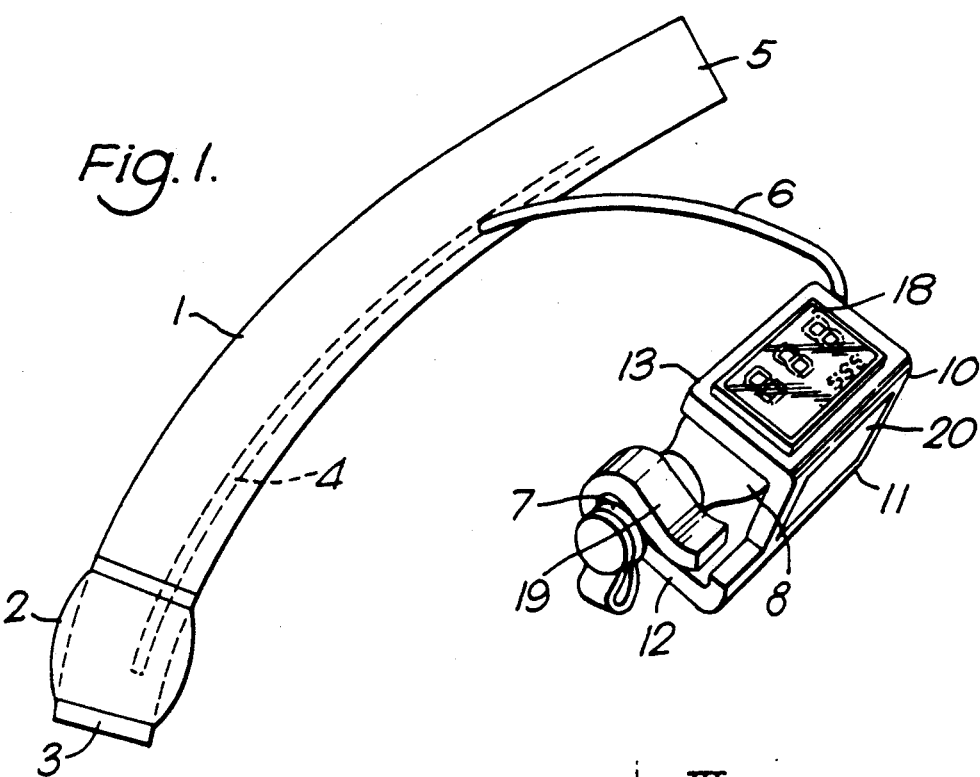
FIG. 1 is a side elevation view of the assembly.

With reference first to FIG. 1, there is shown a conventional cuffed endotracheal tube 1 having an inflatable cuff 2 extending around the tube close to its patient end 3. The interior of the cuff 2 communicates with an inflation lumen 4 extruded along the length of the tube 1 within its wall. Towards the machine end 5 of the tube, one end of an inflation line 6 is connected into the lumen 4. The inflation line 6 is flexible and, in use extends out of the patient's mouth. At its other end, the inflation line 6 has a coupling 7, which may include a valve (not shown), and an inflation indicator 8 in the form of a flexible balloon or envelope sealed to one end of the coupling. The interior of the inflation indicator 8 communicates with the inflation line 6 and cuff 2 so that the indicator 8 is inflated when the cuff 2 is inflated. As so far described, the tube is conventional.

Figure 2:
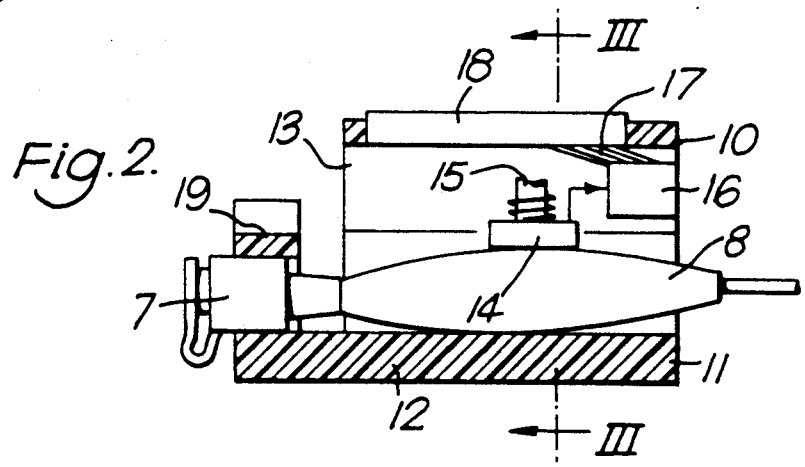
FIG. 2 is a sectional side elevation view of the monitor to a larger scale.
Figure 3:
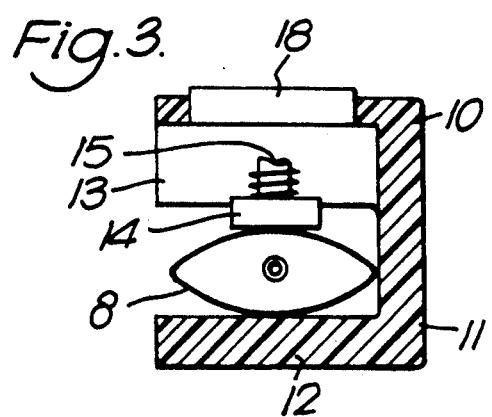
FIG. 3 is a transverse section along the line III—III of FIG. 2.

With reference now also to FIGS. 2 and 3, the pressure monitor 10 is removably clipped onto the outside of the coupling 7 at the machine end of the inflation line 6 and encompasses the inflation indicator 8. The pressure monitor 10 is contained in a plastic housing 11 of U-shape in section which has a flat base-plate 12 and an upper assembly 13 spaced from the base-plate by a short distance. The upper assembly 13 includes an electrical pressure sensor 14, such as one including a silicon strain gauge, which is carried on a resilient, spring support 15 and projects downwardly towards the base-plate 12. The electrical output of the pressure sensor 14 is supplied to a processor 16 which performs various conventional calibration, scaling and calculation operations on its input and provides display driver signals on line 17 to a multi-segment liquid crystal display LCD 18. Other displays could be used.

To the left of the upper assembly 13, the housing 11 is formed into a spring clip 19 which overlies and projects downwardly towards the base plate 12. The pressure monitor 10 also has a panel 20 on its side on which can be written pressure readings taken at different times. Alternatively, each pressure reading could be stored electronically within the processor 16.

In use, the pressure monitor 10 is clipped onto the coupling 7, so that the spring clip 19 firmly locates on the coupling, and so that the inflation indicator 8 lies between the base plate 12 and the upper assembly 13. The pressure sensor 14 is urged vertically downwards by the support 15 to contact the upper surface of the exterior of the inflation indicator 8. The output of the pressure sensor 14 depends on the pressure within the inflation indicator 8, and hence on the pressure within the cuff 2.

The pressure monitor 10 can be clipped onto the coupling and inflation indicator either before or after the cuff 2 is inflated, following intubation into the trachea. The display 18 can provide an indication of pressure in the cuff 2 on any standard pressure scale, or on an arbitary numeric scale. Alternatively, the indication of pressure could be provided on a non-numerical display, such as, for example, a bar graph display. Preferably each tube has its own pressure monitor 10 which is clipped in place when the tube is inserted and remains in place until the tube is removed. The nurse or anaesthetist can check the pressure reading periodically and, if the cuff pressure is too low or high, air can be inserted into or withdrawn from the cuff using a syringe inserted into the coupling 7 in the usual way. This operation of correcting the pressure in the cuff can be carried out while the monitor is in place. Alternatively, the pressure monitor 10 could be carried around in the pocket of the nurse or other user and clipped in place on different tubes as and when they are being checked. The pressure monitor 10 could include a visual or audible alarm that signals when the cuff pressure exceeds predetermined limits.

The pressure monitor is not limited to use on tracheal tubes but could be used on other medico-surgical tubes having a cuff that is inflated to seal the tube with the body cavity and a flexible inflation indicator communicating with the cuff.

What we claim is:

1. A cuffed medico-surgical tube assembly including a cuff pressure monitor and a cuffed medico-surgical tube for insertion into a body cavity and having a flexible inflation indicator located externally of the body which communicates with the cuff and is inflated on inflation of the cuff, the pressure monitor having an electrical pressure sensor adapted to provide an output and a display on which is provided a representation indicative of pressure in the cuff, the monitor having means for supporting both the pressure sensor and the display closely adjacent the inflation indicator with the electrical pressure sensor contacting an exterior area of the inflation indicator and with the display being located in a region of the inflation indicator such that a change in inflation of the inflation indicator changes the output of the pressure sensor which causes a change in the representation provided by the display, the pressure monitor including means for resiliently urging the pressure sensor into contact with an opposite side of the infiltration indicator.

2. An assembly according to claim 1, wherein the pressure monitor is removable from the inflation indicator.

3. An assembly according to claim 1, wherein the inflation indicator has a coupling at one end, and wherein the pressure monitor includes a clip that fastens onto an outside of the coupling.

4. An assembly according to claim 1, wherein the pressure monitor includes a base plate that extends along one side of the inflation indicator, and the pressure monitor includes a spring for resiliently urging the pressure sensor into contact with an opposite side of the inflation indicator.

5. An assembly according to claim 1, wherein the electrical pressure sensor includes a silicon strain gauge.

6. An assembly according to claim 1, wherein the display is a numeric display.

7. An assembly according to claim 1, wherein the display is a liquid crystal display.

8. A cuffed medico-surgical tube assembly including a cuff pressure monitor and a cuffed tracheal tube having a flexible balloon inflation indicator mounted at one end of an inflation line communicating with a cuff on the tracheal tube, a coupling mounted at one end of the inflation indicator by which gas can be supplied to or from the cuff, the pressure monitor comprising an electrical pressure sensor mounted for contact with one side of the inflation indicator so that a change in pressure within the inflation indicator causes a change in an output of the pressure sensor, said pressure monitor further comprising an electrical display and means coupling the output of the pressure sensor to the display so that the display provides a display representation of pressure in the cuff, and means securing the pressure monitor and its sensor and display with said coupling so that said display representation is provided in a region of the inflation indicator, the pressure monitor including means for resiliently urging the pressure sensor into contact with an opposite side of the infiltration indicator.

* * * * *